(12) United States Patent
Hawkins et al.

(10) Patent No.: US 9,012,416 B2
(45) Date of Patent: Apr. 21, 2015

(54) TOBRAMYCIN FORMULATION

(71) Applicant: Norton Healthcare Limited, Castleford, West Yorkshire (GB)

(72) Inventors: Kevin Hawkins, Runcorn (GB); David Higham, Runcorn (GB)

(73) Assignee: Norton Healthcare Limited, West Yorkshire (GB)

( * ) Notice: Subject to any disclaimer, the term of this patent is extended or adjusted under 35 U.S.C. 154(b) by 59 days.

(21) Appl. No.: 13/847,265

(22) Filed: Mar. 19, 2013

(65) Prior Publication Data

US 2013/0303475 A1 Nov. 14, 2013

Related U.S. Application Data

(60) Provisional application No. 61/644,700, filed on May 9, 2012.

(30) Foreign Application Priority Data

May 9, 2012 (GB) .................................. 1208080.0

(51) Int. Cl.
*A01N 43/04* (2006.01)
*A61K 31/70* (2006.01)
*A61K 31/7036* (2006.01)
*A61K 9/00* (2006.01)
*A61K 47/12* (2006.01)
*A61K 9/08* (2006.01)
*A61K 47/02* (2006.01)

(52) U.S. Cl.
CPC ............ *A61K 31/7036* (2013.01); *A61K 9/0078* (2013.01); *A61K 47/12* (2013.01); *A61K 9/08* (2013.01); *A61K 47/02* (2013.01)

(58) Field of Classification Search
None
See application file for complete search history.

(56) References Cited

U.S. PATENT DOCUMENTS

| 7,795,316 B1 * | 9/2010 | Kabra ........................... 424/659 |
| 2007/0071686 A1 | 3/2007 | Lintz et al. |

FOREIGN PATENT DOCUMENTS

| CN | 1760212 A | 4/2006 |
| CN | 1927201 A | 3/2007 |
| EP | 1683526 A1 | 7/2006 |
| EP | 2062581 A1 | 5/2009 |
| EP | 2062585 A1 | 5/2009 |
| WO | WO-96/12471 A1 | 5/1996 |
| WO | WO-02/094217 A1 | 11/2002 |
| WO | WO-03/004005 A1 | 1/2003 |
| WO | WO-2005/037256 A2 | 4/2005 |
| WO | WO 2006120705 A2 | 11/2006 |
| WO | WO 2008130211 A1 | 10/2008 |
| WO | WO 2011162752 A1 | 12/2011 |

OTHER PUBLICATIONS

Ratjen et al. The Lancet (2001), vol. 358, pp. 983-984.*
Extended European Search Report corresponding to EP 13002039 dated Jun. 19, 2013, 5 pp.
Bryan Dotson et al., Physical compatibility of 4% sodium citrate with selected antimicrobial agents, American Journal of Health-system Pharmacy, Jul. 15, 2010, vol. 67, No. 14, pp. 1195-1198.

* cited by examiner

*Primary Examiner* — Patrick Lewis
(74) *Attorney, Agent, or Firm* — RatnerPrestia

(57) ABSTRACT

This invention provides a pharmaceutical solution formulation comprising tobramycin, water, sodium chloride and sodium citrate, wherein the formulation has a pH of 4.5-7.0 and an osmolality of 135-200 mOsmol/Kg.

19 Claims, No Drawings

TOBRAMYCIN FORMULATION

CROSS-REFERENCE TO RELATED APPLICATIONS

This application claims priority of U.S. Provisional Application No. 61/644,700, filed May 9, 2012, and British Patent Application No. 1208080.0, filed May 9, 2012, the disclosures of both of which are incorporated herein by reference in their entireties for all purposes.

FIELD OF THE INVENTION

The present invention relates to a tobramycin formulation and particularly to a pharmaceutical solution formulation of tobramycin for inhalation.

BACKGROUND OF THE INVENTION

Tobramycin is an aminoglycoside antibiotic specifically active against *Pseudomonas aeruginosa*. It is indicated for the long-term management of chronic pulmonary infection due to *Pseudomonas aeruginosa* in cystic fibrosis (CF) patients aged 6 years and older.

Tobramycin may be administered parenterally for the treatment of chronic pulmonary infection. However, aminoglycoside penetration into the bronchial secretions is poor and to achieve a therapeutic concentration in sputum, high doses are required. Such high doses increase the risk of systemic toxicity.

To avoid the problem of toxicity via parenteral administration, tobramycin may also be administered via inhalation. The preferred approach for administration by inhalation for tobramycin is by nebulisation of an aqueous solution of the tobramycin. Typically, active ingredients are dissolved in saline for nebulisation. However, jet and ultrasonic nebulisers are highly sensitive to the osmolality of the formulation and hence careful control of the tonicity is required. Moreover, cystic fibrosis patients and other patients with chronic endobronchial infections are sensitive to hypo- or hypertonic aerosols.

Tobramycin is marketed in the EU as TOBI®. TOBI® is sold in the form of a 300 mg/5 mL nebuliser solution. One 5 mL nebule contains tobramycin 300 mg as a single dose. It is supplied for use via inhalation. TOBI® contains tobramycin, sodium chloride, water for injection, and sulfuric acid/sodium hydroxide for pH adjustment. The concentration of sodium chloride in the formulation is 2.25 mg/mL.

Further discussion of the formulation may be found in WO 96/12471. WO 96/12471 describes aminoglycoside formulations formulated in about 5 mL of water, wherein the solution contains about 0.225% w/v of sodium chloride. This document also explains the importance of carefully controlling the concentration of the sodium chloride in order to provide correct nebulisation and to avoid bronchospasm in patients sensitive to hypo- or hypertonic aerosols.

WO02/094217, WO 03/004005 and WO 2005/037256 also discuss the importance of carefully controlling the amount of sodium chloride present in the formulation.

A further difficulty in formulating tobramycin is that tobramycin formulations tend to be chemically unstable. TOBI® is supplied with special precautions for storage, namely that it should be stored at 2-8° C. in its original packaging and protected from sunlight. Some yellowing of the formulation also occurs.

WO 96/12471 is not specifically concerned with addressing the problem of storage stability. However, it does explain that the formulation should be treated by nitrogen sparging (see the paragraph bridging pages 15 and 16) in order to minimise hydrolysis and oxidative degradation.

However, there remains a need in the art for chemically stable tobramycin formulations which are capable of being administered by inhalation. The present invention addresses this and other problems with the prior art.

DETAILED DESCRIPTION OF THE INVENTION

Accordingly, the present invention provides a pharmaceutical solution formulation comprising tobramycin, water, sodium chloride and sodium citrate, wherein the formulation has a pH of 4.5-7.0 and an osmolality of 135-200 mOsmol/Kg.

This formulation provides an excellent stability profile without compromising the precise range of osmolality required for formulations which are to be administered by nebulisation.

The active substance in the formulation is the aminoglycoside antibiotic, tobramycin. Tobramycin is specifically active against *Pseudomonas aeruginosa*. The tobramycin is preferably present in an amount of 4.0 to 8.0% w/v, more preferably 5.0 to 7.0% w/v, most preferably about 6.0% w/v, based on the total volume of the formulation. This equates to an amount of tobramycin of 40-80 mg/mL, 50-70 mg/mL, and about 60 mg/mL, respectively. The formulation preferably has a total volume of 5 mL and is most preferably presented in the form of 5 mL solution containing 300 mg tobramycin.

The formulation is an aqueous formulation and further comprises water. The water is preferably water for injection.

The sodium chloride is preferably present in an amount of less than 0.15% w/v, based on the total volume of the formulation. The minimum level is defined by the osmolality of the final formulation. Preferably, the sodium chloride is present in an amount of at least 0.05% w/v, based on the total volume of the formulation. A particularly preferred range is 0.09-1.3% w/v, based on the total volume of the formulation.

The formulation also contains sodium citrate. In particular, the presence of sodium citrate minimises the formation of the degradation product, nebramine. In this regard, the present invention also provides a pharmaceutical formulation comprising tobramycin that contains nebramine in an amount of less than 0.07% by weight, preferably less than about 0.06% by weight, more preferably 0.05% by weight or less, having been subjected to 25° C./40% RH for 26 weeks. In one aspect, the present invention provides for the use of sodium citrate for stabilising a pharmaceutical formulation comprising tobramycin.

Surprisingly, it has been found that the level of sodium chloride may be reduced in favour of sodium citrate in order to provide increased chemical stability of the active substance whilst maintaining the appropriate osmolality of the formulation.

In a preferred embodiment, the sodium citrate is present in an amount of 0.05-1.00% w/v, preferably 0.1 to about 0.5% w/v, more preferably 0.2-0.4% w/v and most preferably about 0.3% w/v, based on the total volume of the formulation.

Citric acid is trivalent and the sodium citrate is preferably the trisodium salt. Unless indicated otherwise, reference to "sodium citrate" indicates the mono-, di- or trisodium salts or combinations thereof. Preferably, the sodium citrate used is trisodium citrate. The sodium citrate is typically introduced to the solution as trisodium citrate dihydrate.

The pH of the formulation is adjusted using an acid and/or a base. It is preferably adjusted using sulfuric acid and sodium hydroxide. As concentrations, 10% sulfuric acid and 5M sodium hydroxide are suitable. The final pH is 4.5-7.0, preferably the pH is 5.5-6.5 and most preferably about 6. The pH may be measured using a conventional pH meter at 20° C.

The osmolality of the formulation is 135-200 mOsmol/Kg and the amounts of the ingredients are adjusted accordingly. Preferably the osmolality of the formulation is 165-190 mOsmol/Kg. The osmolality may be measured using a freezing-point depression osmometer, following the procedure set out in the US Pharmacopeia, USP 34, National Formulary 29, 2011, chapter <785>.

In a preferred embodiment, the formulation consists of tobramycin, water, sodium chloride, sodium citrate, sulfuric acid and sodium hydroxide, and preferably consists of 60.0 mg/mL of tobramycin, 1.125 mg/mL of sodium chloride; 3.0 mg/mL of sodium citrate, water, and sulfuric acid and sodium hydroxide qs to pH 6.0, in which the concentrations are based on the total volume of the formulation.

The present invention also provides a process for preparing the formulation as defined herein comprising: combining tobramycin, water, sodium chloride, sodium citrate; and adjusting the pH to 4.5-7.0 and the osmolality to 135-200 mOsmol/Kg. On account of the effect of the sodium citrate, this preparation may be carried out without sparging with an inert gas (e.g. nitrogen).

The formulation described herein may be used for the treatment of *Pseudomonas aeruginosa* infection, particularly in patients with cystic fibrosis. Specifically, it is presently indicated for the long-term management of chronic pulmonary infection due to *Pseudomonas aeruginosa* in cystic fibrosis (CF) patients aged 6 years and older. The formulation is suitable for inhalation and preferably the treatment is by inhalation. Most preferably, the formulation is administered using a nebuliser, e.g. a jet or ultrasonic nebuliser. These nebulisers deliver the formulation as an aerosol. Typically the aerosol has a particle size of 1-5 µm which is ideal for treatment by inhalation. Accordingly, the present invention also provides a nebule containing the formulation as defined herein.

The present invention will now be described with reference to the accompanying examples, which are not intended to be limiting.

EXAMPLES

Example 1

A 5 mL formulation of the present invention was prepared by combining the following components (see Table 1):

TABLE 1

Formulation of the present invention.

| Component | Per mL | % w/v |
|---|---|---|
| Tobramycin | 60 mg | 6.0 |
| Sodium chloride | 1.125 mg | 0.1125 |
| Trisodium citrate dihydrate | 3.0 mg | 0.30 |
| 10% Sulfuric acid | q.s. to pH 6.0 | q.s. to pH 6.0 |
| Sodium hydroxide 5M | | |
| Water for injections, Ph. Eur | q.s. to 1 mL | q.s. to 100% |

The osmolality of the solution was 170 mOsmol/Kg.

Example 2

The stability of formulations prepared according to the present invention was compared against the commercial formulation, TOBI®. TOBI® has the following formulation (see Table 2):

TABLE 2

Comparative formulation (TOBI ®).

| Component | Per mL | % w/v |
|---|---|---|
| Tobramycin | 60 mg | 6.0 |
| Sodium chloride | 2.25 mg | 0.225 |
| 10% Sulfuric acid | q.s. to pH 6.0 | q.s. to pH 6.0 |
| Sodium hydroxide 5M | | |
| Water for injections, Ph. Eur | q.s. to 1 mL | q.s. to 100% |

Tests were carried out in which each formulation was stored at 25° C./40% RH for 26 weeks. Both the level of nebramine and the absorbance of the formulations were measured. Absorbance is a measure of the opacity of the formulation following storage. The higher the level of degradation/presence of impurities, the greater the opacity of the formulation. The results are presented in the table hereinbelow (Table 3):

TABLE 3

Stability data of the comparative formulation and formulation of the present invention.

| Formulation | Batch | Absorbance (AU) | Nebramine (%) |
|---|---|---|---|
| TOBI ® | 4.1 | 0.20 | 0.09 |
| (Sodium chloride | 4.2 | 0.19 | 0.09 |
| 2.25 mg/mL) | 4.3 | 0.18 | 0.08 |
| | 4.4 | 0.16 | 0.07 |
| Example 1 | 4.5 | 0.14 | 0.04 |
| (Sodium chloride | 4.6 | 0.13 | 0.04 |
| 1.125 mg/mL/ | 4.7 | 0.15 | 0.05 |
| sodium citrate 3.0 mg/mL) | 4.8 | 0.13 | 0.04 |

It is clearly seen from the results in the table above that the presence of sodium citrate reduces the levels of both absorbance and nebramine after storage. Thus, the presence of sodium citrate is shown to improve stability of a tobramycin formulation.

Example 3

A study was conducted to demonstrate that a tobramycin nebuliser solution according to the present invention is equivalent to the commercial formulation in terms of delivery rate, total active substance delivered and droplet size distribution of the nebulised aerosol.

Data generated within the study were evaluated statistically based upon the industry guidance. The results demonstrated that for all parameters tested the products were statistically equivalent. The methodology and results are detailed hereinbelow.

(i) Active Substance Delivery Rate and Total Active Substance Delivered

The method used to determine active substance delivery rate and total active substance delivered involved use of a breathing simulator. A summary of the test results is provided in the following Tables 4 and 5:

TABLE 4

Active substance delivery rate for adult and child breathing profiles.

| | Parameter | Adult | Child |
|---|---|---|---|
| Reference | Range (% mean) | 85.2-115.6 | 67.4-122.6 |
| Test | Range (% mean) | 84.4-117.2 | 69.6-124.4 |

TABLE 5

Total active substance delivered for adult and child breathing profiles.

| | Parameter | Adult | Child |
|---|---|---|---|
| Reference | Range (% mean) | 83.4-109.9 | 80.8-113.4 |
| Test | Range (% mean) | 79.8-110.7 | 82.8-115.7 |

A summary of a statistical evaluation demonstrating product equivalence is provided in Tables 6 and 7.

TABLE 6

Statistical analysis of active substance delivery rate for adult and child breathing profiles.

| Parameter | Ratio (T/R)% | Equivalent (Yes/No) |
|---|---|---|
| Adult | 100.0 | Yes |
| Child | 100.2 | Yes |

TABLE 7

Statistical analysis of total active substance delivered for adult and child breathing profiles.

| Parameter | Ratio (T/R)% | Equivalent (Yes/No) |
|---|---|---|
| Adult | 102.2 | Yes |
| Child | 98.6 | Yes |

The studies therefore concluded that the tobramycin nebuliser solution 300 mg/5 mL according to the present invention and the commercial product are equivalent for the active substance delivery rate and total active substance delivered at breath profiles representative of child and adult breathing patterns.

(ii) Droplet Size Distribution of the Nebulised Aerosol

A summary of the test results is provided below in Table 8.

TABLE 8

Droplet size distribution of the nebulised aerosol.

| | Parameter | Dv[10] | Dv[50] | Dv[90] | Span |
|---|---|---|---|---|---|
| Reference | Range (% mean) | 67.2-128.1 | 93.2-112.0 | 89.3-118.6 | 92.3-119.2 |
| Test | Range (% mean) | 70.4-121.1 | 91.8-108.0 | 87.1-132.2 | 91.9-124.1 |

A summary of a statistical evaluation demonstrating product equivalence is provided in Table 9:

TABLE 9

Statistical analysis for droplet size distribution of the nebulised aerosol.

| Parameter | Ratio (T/R)% | Equivalent (Yes/No) |
|---|---|---|
| Dv[10] | 103.5 | Yes |
| Dv[50] | 100.7 | Yes |

TABLE 9-continued

Statistical analysis for droplet size distribution of the nebulised aerosol.

| Parameter | Ratio (T/R)% | Equivalent (Yes/No) |
|---|---|---|
| Dv[90] | 102.0 | Yes |
| Span | 101.2 | Yes |

The studies therefore conclude that the tobramycin nebuliser solution 300 mg/5 mL according to the present invention and the commercial product are equivalent for the droplet size distribution of the nebulised aerosol.

What is claimed:

1. A pharmaceutical solution formulation comprising tobramycin, water, sodium chloride and sodium citrate, wherein the formulation has a pH of 4.5-7.0 and an osmolality of 135-200 mOsmol/Kg.

2. A formulation as claimed in claim 1, wherein the tobramycin is present in an amount of 4.0 to 8.0% w/v.

3. A formulation as claimed in claim 1, wherein the sodium chloride is present in an amount of less than 0.15% w/v.

4. A formulation as claimed in claim 1, wherein the sodium citrate is present in an amount of 0.05-1.00% w/v.

5. A formulation as claimed in claim 1, wherein the pH is adjusted using sulfuric acid and sodium hydroxide.

6. A formulation as claimed in claim 1 consisting of tobramycin, water, sodium chloride, sodium citrate, sulfuric acid and sodium hydroxide.

7. A formulation as claimed in claim 1 consisting of 60.0 mg/mL of tobramycin, 1.125 mg/mL of sodium chloride; 3.0 mg/mL of sodium citrate, water, and sulfuric acid and sodium hydroxide qs to pH 6.0.

8. A formulation as claimed in claim 1, wherein the total volume of the formulation is 5 mL.

9. A formulation as claimed in claim 1, for the treatment of *Pseudomonas aeruginosa* infection.

10. A formulation as claimed in claim 9, wherein the treatment is by inhalation.

11. The formulation as claimed in claim 1 contained in a nebule.

12. A process for preparing the formulation as claimed in claim 1, comprising: combining tobramycin, water, sodium chloride, sodium citrate; and adjusting the pH to 4.5-7.0 and the osmolality to 135-200 mOsmol/Kg.

13. A process as claimed in claim 12, wherein the preparation is carried out without sparging with an inert gas.

14. A method of stabilizing a pharmaceutical formulation comprising tobramycin comprising combining sodium citrate with the formulation.

15. A formulation as claimed in claim 9 for treatment of patients with cystic fibrosis.

16. A method of treating *Pseudomonas aeruginosa* infection comprising administering to a patient in need of such treatment a formulation as claimed in claim 1.

17. A method of treating cystic fibrosis comprising administering to a patient in need of such treatment a formulation as claimed in claim 1.

18. A formulation as claimed in claim 1, wherein the formulation has less than 0.7% by weight nebramine after twenty six weeks of storage at 25° Celcius and 40% relative humidity.

19. A process as claimed in claim 12, wherein the osmolality is adjusted to 165-190 mOsmol/Kg.

* * * * *